US00RE38797E

(19) United States
(12) Reissued Patent
Linker et al.

(10) Patent Number: US RE38,797 E
(45) **Date of Reissued Patent: *Sep. 20, 2005**

(54) PARTICLE PRECONCENTRATOR

(75) Inventors: Kevin L. Linker, Albuquerque, NM (US); Frank J. Conrad, Russellville, SC (US); Chad A. Custer, Albuquerque, NM (US); Charles L. Rhykerd, Jr., Albuquerque, NM (US)

(73) Assignee: Sandia National Laboratories, Albuquerque, NM (US)

( * ) Notice: This patent is subject to a terminal disclaimer.

(21) Appl. No.: 10/189,093

(22) Filed: Jul. 3, 2002

Related U.S. Patent Documents

Reissue of:
(64) Patent No.: 6,085,601
Issued: Jul. 11, 2000
Appl. No.: 09/170,865
Filed: Oct. 13, 1998

U.S. Applications:
(62) Division of application No. 08/988,542, filed on Dec. 10, 1997, now Pat. No. 5,854,431.

(51) Int. Cl.[7] ..... G01N 1/00
(52) U.S. Cl. ..... 73/863.12; 73/863.23
(58) Field of Search ..... 73/31.01, 31.02, 73/31.07, 28.04, 863.12, 863.21, 863.23, 864.34, 864.81, 864.11, 864.73, 28.03; 250/288; 422/88; 55/282.2, 315.1, 341.7, 467.1, 525, 428.1, 428; 96/413

(56) References Cited

U.S. PATENT DOCUMENTS

| | | | |
|---|---|---|---|
| 1,174,631 | A | 3/1916 | Snelling |
| 3,140,936 | A | 7/1964 | Schwartz |
| 3,417,548 | A | 12/1968 | Thompson |
| 3,578,757 | A | 5/1971 | Samuilov |

(Continued)

FOREIGN PATENT DOCUMENTS

WO WO 94/14608 7/1994

OTHER PUBLICATIONS

McGann et al., Development of a New Portal Explosives Vapor Detection System, Monthly Report No. 8 (Sep. 1992).
McGann et al., Development of a New Portal Explosives Vapor Detection System, Monthly Report No. 10 (Oct. 1992).
Answer and Counter Claim, Sandia Corp. and Barringer Instruments, Inc. v. Ion Track Instruments LLC and Ion Track Inc.
John E. Parmeter, Kevin L. Linker, Charles Rhykerd, Jr. and David W. Hannum, "*Testing Of A Walk–Through Portal For The Trace Detection Of Contraband Explosives*", Proceedings of the Second Explosives Detection Technology Symposium & Aviation Security Conference held Apr. 1997; pp. 187–192.

(Continued)

*Primary Examiner*—Robert Raevis
(74) *Attorney, Agent, or Firm*—Lowenstein Sandler PC

(57) ABSTRACT

An apparatus and method for preconcentrating particles and vapors. The preconcentrator apparatus permits detection of highly diluted amounts of particles in a main gas stream, such as a stream of ambient air. A main gas stream having airborne particles entrained therein is passed through a pervious screen. The particles accumulate upon the screen, as the screen acts as a sort of selective particle filter. The flow of the main gas stream is then interrupted by diaphragm shutter valves, whereupon a cross-flow of carrier gas stream is blown parallel past the faces of the screen to dislodge the accumulated particles and carry them to a particle or vapor detector, such as an ion mobility spectrometer. The screen may be heated, such as by passing an electrical current there through, to promote desorption of particles therefrom during the flow of the carrier gas. Various types of screens are disclosed. The apparatus and method of the invention may find particular utility in the fields of narcotics, explosives detection and chemical agents.

33 Claims, 3 Drawing Sheets

U.S. PATENT DOCUMENTS

| | | | | | |
|---|---|---|---|---|---|
| 3,695,003 | A | | 10/1972 | Bednarski | |
| 3,748,905 | A | | 7/1973 | Fletcher et al. | |
| 4,117,715 | A | * | 10/1978 | Hoenig | 73/28.01 |
| 4,154,664 | A | * | 5/1979 | Renevot | 204/410 |
| 4,205,550 | A | | 6/1980 | Swanson | |
| 4,242,107 | A | | 12/1980 | Jenkins | |
| 4,251,238 | A | | 2/1981 | Claes et al. | |
| 4,885,078 | A | * | 12/1989 | Spengler et al. | 204/424 |
| 4,906,973 | A | | 3/1990 | Karbowski et al. | |
| 4,942,135 | A | | 7/1990 | Zaromb | |
| 4,964,309 | A | | 10/1990 | Jenkins | |
| 4,977,095 | A | | 12/1990 | Zaromb | |
| 4,987,767 | A | | 1/1991 | Corrigan et al. | |
| 5,083,019 | A | | 1/1992 | Spangler | |
| 5,092,218 | A | | 3/1992 | Fine et al. | |
| 5,109,691 | A | | 5/1992 | Corrigan et al. | |
| 5,138,889 | A | | 8/1992 | Conrad | |
| 5,142,143 | A | | 8/1992 | Fite et al. | |
| 5,162,652 | A | | 11/1992 | Cohen et al. | |
| 5,173,264 | A | | 12/1992 | Zaromb et al. | |
| 5,206,592 | A | | 4/1993 | Buess et al. | |
| 5,233,300 | A | | 8/1993 | Buess et al. | |
| 5,289,715 | A | | 3/1994 | Staples et al. | |
| 5,300,758 | A | | 4/1994 | Rounbehler et al. | |
| 5,310,681 | A | | 5/1994 | Rounbehler et al. | |
| 5,328,851 | A | | 7/1994 | Zaromb | |
| 5,345,809 | A | | 9/1994 | Corrigan et al. | |
| 5,395,589 | A | | 3/1995 | Nacson | |
| 5,405,781 | A | | 4/1995 | Davies et al. | |
| 5,465,607 | A | | 11/1995 | Corrigan et al. | |
| 5,585,575 | A | | 12/1996 | Corrigan et al. | |
| 5,886,249 | A | * | 3/1999 | Bonne et al. | 73/24.02 |

OTHER PUBLICATIONS

P.J. Thomas, J.M. May, D. E. Elisco and Frank Conrad, "*Explosives Vapor Preconcentrator*", Proceedings of New Concepts Symposium and Workshop On Detection and Identification of Explosives, Oct. 30–Nov. 1, 1978 Reston, VA., p. 81.

Ion Track Instruments, LLC and Ion Track, Inc.'s Response to Sandia Corporation, Barringer Instruments, Inc., and Frank J. Conrad's First Set of Interrogatories, Sep. 9, 2002.

Ion Track Instruments, LLC and Ion Track, Inc.'s Supplemental Response to Sandia Corporation, Barringer Instruments, Inc., and Frank J. Conrad's First Set of Interrogatories, Oct. 16, 2002.

Answer to Counterclaim (USDC–Dist. of NJ) Civil Action No. 02–1692 (MLC) (Plaintiff Sandia Corp. responding to Counterclaim of Defendant ION Track Instruments, LLC and ION T rack, Inc.).

First Amended Answer & Counter Claim (USDC–Dist. of NJ) Civil Action No. 02–1692 (MLC) (Plaintiff Sandia Corp. Defendant ION Track Instruments, LLC and ION T rack, Inc.).

Douglas R Adkins, Timothy A. Moss, Charles E. Andraka, Nicos H. Andreas, and Howard H. Cole, "*An Examination of Metal Felt Wicks for Heat Pipe Applications*" Reprint from Solar Engineers, Book No. H0932A– 1995, pp. 553–558.

Bekaert Fibre Technologies, "*Leading The World In Metal Fibre Technology For Filtration*", no date.

Bekaert Fibre Technologies, "*Bekipor—Porous Metal Fibre Media—High Performance Through Technology*," no date.

Bekaert—"*Bekaert Advanced Filtration—The Ultimate Filter Innovation*", no date.

Bekaert Corporation Letterhead—"*Bekipor ST BL3 Filter Medium—Product Specifications and Remarks*, " no date.

Frank J. Conrad, B.T.Kenna, D.H. Hannum, "*Current Explosives Technology at Sandia National Laboratories*", 33$^{rd}$ INNM Annual Meeting, Jul. 19–23, 1992, pp. 932–935.

B.T. Kenna, F.J. Conrad, D.W. Hannum, "*Explosive Vapor Emission*, " Proceedings of the First International Symposium on Explosive Detection Technology, Nov. 13–15, 1991 (SAND91–2486C).

John E. Parmeter, Charles E. Rhykerd, Jr., Kevin L. Linker, and David W. Hannum, Bureau of Alcohol, Tobacco and Firearm Explosive Symposium, Wash., D.C., Sep. 20, 1995, "*Explosives Vapor Detection Portal Development At Sandia National Laboratories*, " (SAND95–2276C).

John E. Parmeter, Christian M. Lastoskie, Frank J. Conrad, David W. Hannum and Kevin L. Linker, 11$^{th}$ Annual Security Technology Symposium & Exhibition, Jun., 1995, Virginia Beach, VA, "*The Development of a Walk–Through Portal Detector For The Identification Of Contraband Explosives*, " SAND95–1441C.

F.J. Conrad, T.A. Burrows and W. David Williams, "*Selection of a Gas Chromatographic Material for Use In Explosives Vapor Preconcentration*, " (1979) pp. 1–15 SAND78–1246.

F.J. Conrad, T.A. Burrows and W. David Williams, "*Selection of a Gas Chromatographic Material For Use In Explosives Vapor Preconcentration*, " Journal of Chromatography, 176 (1979) pp. 37–41 SAND78–1246.

Bernard, T. Kenna, Frank J. Conrad, "*Studies of the Adsorption/Desorption Behavior of Explosive–Like Molecules*, " Oct. 1989 SAND 86–0141.

W. David Williams, Lester L. Sandlin, and Frank J. Conrad, "*Laboratory Evaluation of Five Commercial Electron capture–Type Explosives Vapor Detectors*, " Jun., 1978 SAND78–0245.

John E. Parmeter and Chad A. Custer, "*Development of a Portable Preconcentrator/Ion Mobility Spectrometer System For the Trace Detection Of Narcotics*, " Aug., 1997 SAND97–2037.

R.L. Schellenbaum and D.W. Hannum, "*Laboratory Development of the PCP large Reaction Volume Ion Mobility Spectrometer* (*LRVIMS*), " Mar., 1990 SAND89–0461.

Civil Action No. 02–1692 (MLC) *Sandia Corporation and Barringer Instruments* v. *Ion Track Instruments*—Index of Deposition Transcripts in Chronological Order: Frank J. Conrad, Sep. 24, 2002, pp. 1–262, Frank J. Conrad, Sep. 25, 2002, pp. 263–366, Chad A. Custer, Oct. 1, 2002, pp. 1–244, Charles Rhykerd, Jr., Oct. 2, 2002, pp. 1–240, Russell D. Elliott, Oct. 3, 2002, pp. 1–148, Rod D. Baker, Oct. 3, 2002, pp. 1–26, Kevin L. Linker, Oct. 15, 2002, pp. 1–224, Kevin L. Linker, Oct 6, 2002, pp. 225–397, Johan Saelens, Nov. 5, 2002, pp. 1–232.

* cited by examiner

PARTICLE PRECONCENTRATOR

Matter enclosed in heavy brackets [ ] appears in the original patent but forms no part of this reissue specification; matter printed in italics indicates the additions made by reissue.

This is a division of application No. 08/988,542 filed Dec. 10, 1997, now U.S. Pat. No. 5,854,431.

GOVERNMENT RIGHTS

This invention was made with United States Government support under Contract No. DE-AC04-94AL85000 awarded by the U.S. Department of Energy. The Government has certain rights to this invention.

BACKGROUND OF THE INVENTION

1. Field of the Invention (Technical Field)

The present invention relates generally to the field of particle concentrators, and more particularly to an apparatus for pre-concentrating airborne particles to promote their detection, and specifically to a particle preconcentrator apparatus having improved reliability and durability and especially useful for the detection of compounds such as explosives, illegal drugs, other controlled substances and chemical agents. In this application, as set forth more fully later in this disclosure, the term particle is intended not to exclude vapor.

2. Background Art

The use of explosives by terrorists generates tremendous interest in explosives detection. Development of explosives vapor detectors has been especially rapid during the past few years, with a growing number of ion mobility spectrometry (IMS), electron capture detector, and chemi-luminescence-based systems appearing on the market. Current explosives detection systems are hampered, however, by a need to detect explosives residues at extremely low (in the range of parts-per-trillion, ppt) concentrations, and to do so quickly (on a per person or per item basis) and with minimal invasion of the personal privacy of airline travelers and the like. As a result, a further need has arisen for a vapor particle preconcentrator apparatus, that is, an apparatus which quickly gathers vapor particles occurring in very low concentrations, and concentrates them prior to presenting them to a detecting and/or measuring device. By pre-concentrating the target particles prior to detection, known detection methods such as IMS, electron capture, and chemi-luminescence may be employed for screening purposes despite low environmental concentrations.

One goal, for example, is to detect extremely low concentrations of chemical residues that cling to, but are readily dislodged from, the clothing and/or skin of an individual who has recently handled the chemical (or is actually concealing on his person a bulk quantity of the chemical). Low concentrations of the target particles may even occur in the air immediately about the individual's body. When an individual handles or otherwise comes in contact with a modest quantity of, for example, an explosive or narcotic substance, significant numbers of particles of the substance typically cling feebly to the person's skin and/or clothing. For a period of time thereafter, dry particles or vapors of the substance may be shed or emitted from the person, particularly if a disturbance such as a blowing wind or a jostling bump causes significant numbers of particles to dislodge from the person and become entrained or suspended in the surrounding air. A desirable apparatus for testing for the presence of a target substance on an individual is capable of detecting these "dislodged" particles, permitting detection without the need for physical contact with the individual.

Many known detection devices, however, require the presence of comparatively high concentrations of target substance particles for reliable detection. Known devices employing high-volume air flows to blow or suction particles from a person suffer from particle concentration dilution, rendering detection unreliable. Moreover, known detectors for use in testing for explosives or drugs on humans, luggage, motor vehicles, and other bulky items frequently cannot properly process the large air volumes used to collect the target particles. In such circumstances, a concentrator becomes a necessity. An effective concentrator must effectively collect extremely small quantities (i.e. highly diluted) of particles from a high volume air (or other gas) flow, and then effectively release the collected (i.e. concentrated) particles for transportation to a detector device.

Thus, a goal of particle preconcentration for detection is to efficiently collect (adsorb) as many particles as possible from a large volume, low-concentration sample, and then release (desorb) the concentrated particles to a detector device. Known methods of preconcentration to collect and release particles for detection include volume collection in a bed or filter of charcoal, and thin-foil collectors.

Volume collection involves the adsorption of the target particles in a large absorbent bed, typically a bed of charcoal. Volume collection is a reasonably efficient method of absorption due to the abundance of surface area for a given volume of charcoal bedding. Particle desorption for presentation to the detector, however, is difficult and slow in volume collection systems. A particle preconcentrator based upon volume collection techniques is commercially impracticable for purposes of explosives detection due to the size of the device and the unacceptably large amount of time required to desorb the concentrated particles.

Some known preconcentrator devices utilize adsorption upon the solid surfaces of thin foils. A thin foil preconcentrator includes a collection of thin metallic foils disposed mutually parallel within a plenum. The foils, which may incorporate ultra-thin stainless steel films, are expensive to manufacture. A high-volume discharge of air bearing the low concentration of target particles is blown through the plenum and parallel between the foils. Ostensibly, target particles impact, adhere to, and accumulate upon the confronting planar faces of the foils; desorption is then promoted by heating the foils and blowing clean air parallel between the foils to dislodge accumulated particles and transport them to a detector.

Obtaining the needed surface area for particle collection in a thin foil preconcentrator can result in a physically large unit with excessive dead space or, conversely, very closely-spaced foils. To provide adequate electrical resistance in the foils to heat them during desorption, the foils must be very thin. The high-volume air flow necessary for rapid adsorption frequently causes tearing, displacement, and destruction of the thin, fragile, foils, a problem aggravated when the foils are closely spaced, thereby impeding the discharge. Discharges sufficiently lowered to reduce foil damage, and which are desirable in the desorption stage, may not be strong enough to release accumulated particles from the foil faces. Additionally, because the sample-bearing air stream blows parallel past the foils, a boundary layer forms on the foil surfaces, impeding the impact and adhesion of particles upon the foils. If a significantly large item, e.g., handkerchief, comb, pencil, or the like, should be ingested by the preconcentrator, the foils are susceptible to severe damage and loss of collection surface area. Such ingestion is a concern with actual field applications of explosive and narcotic detection.

Another known surface collection method of preconcentration is the use of a membrane filter preconcentrator. Similar to the volume collection method, the membrane filter method is very efficient for absorption of vapors and particles because of the large surface area to volume ratio. The membrane filter, however, lacks the ability to quickly desorb the vapors and particles from the surface as does the volume collection method.

A need remains, therefore, for a preconcentrator device that functions rapidly and is durable for field use, such for use within explosives detectors within airport terminals and the like.

SUMMARY OF THE INVENTION (DISCLOSURE OF THE INVENTION)

The invention relates to a method and apparatus for performing preconcentration of dilute particles in a moving gas stream. The invention has particular application to efforts to collect and detect trace quantities of contraband substances such as illicit drugs, explosives and chemical agents but may find utility in laboratory research and other fields such as environmental monitoring.

According to the invention, there is provided an apparatus for collecting particles entrained in a moving first gas stream, the apparatus comprising at least one pervious screen disposed across the first gas stream, whereby the first gas stream passes through the screen and at least some of the particles are caught by the screen, means for interrupting the passage of the first gas stream through the at least one screen, means for generating a cross-flow of a carrier gas stream parallel past the at least one screen, whereby particles caught upon the screen are entrained into the carrier gas stream, and means for detecting particles in the carrier gas stream. The apparatus may further comprise means for inducing the first gas stream movement. The first gas stream may be ambient air, and the means for inducing the first gas stream movement may be a fan. The means for interrupting the passage of the first gas stream preferably comprises a diaphragm shutter. The means for generating a cross-flow of a carrier gas stream preferably comprises a carrier gas inlet valve and a carrier gas outlet valve. The at least one pervious screen may comprise a plurality of substantially parallel screens, and the preferred embodiment further comprises means for heating the at least one screen. The at least one screen preferably comprises an electrically conductive screen and the means for heating preferably comprises means for supplying electric current in the screen. The screen may be a woven wire mesh, or may be a sheet of metallic felt. The detector may be an ion mobility spectrometer.

Also according to the invention there is provided an apparatus for concentrating vapor particles entrained in a moving air stream, the apparatus comprising at least one pervious screen disposed substantially perpendicularly to the air stream, whereby the air stream passes through the screen and at least some of the particles are caught upon the screen, means for interrupting the passage of the air stream through the at least one screen, means for heating the at least one screen, and means for generating a carrier gas stream cross-flow past the at least one screen, whereby particles caught upon the screen are entrained into the carrier gas stream. The apparatus may further comprise a fan for inducing the movement in the air stream. The means for interrupting the passage of the air stream preferably comprises at least one diaphragm shutter. Preferably, the means for generating a cross-flow of a carrier gas stream comprises a carrier gas outlet valve comprising a diaphragm shutter. The at least one pervious screen may comprise a plurality of substantially parallel screens, and the invention preferably also includes means for heating the one or more screens. The screen preferably comprises an electrically conductive screen and the means for heating comprises means for supplying electric current in the screen. The screen may comprise woven wire mesh, or may be a sheet of metallic felt. The apparatus of the invention preferably also includes means for detecting vapor particles entrained in the carrier gas stream, and the means for detecting may be an ion mobility spectrometer.

Also according to the present invention, there is provided a method for collecting and releasing vapors and particles entrained in a moving first gas stream. The method comprises: disposing across the first gas stream at least one pervious screen, whereby the first gas stream passes through the screen and at least some of the particles are caught upon the screen; interrupting the passage of the first air stream through the at least one screen; after interrupting the passage of the first gas stream, generating a cross-flow of a carrier gas stream parallel past the least one screen, whereby particles caught upon the screen are entrained into the carrier gas stream; and directing the carrier gas stream to a detector. The method may further comprise inducing the movement in the first gas stream. Inducing the movement in the first gas stream may comprise blowing ambient air with a fan. Interrupting the passage of the first gas stream comprises closing a valve, such as actuating a diaphragm shutter.

Generating a cross-flow of a carrier gas stream preferably comprises opening a carrier gas inlet valve in a carrier gas duct, and opening a carrier gas outlet valve. Opening a carrier gas outlet valve preferably comprises opening a diaphragm shutter, gate valve or ball valve. Disposing at least one pervious screen may comprise disposing parallel a plurality of screens. The method of the invention preferably includes heating the at least one screen after generating a cross-flow of a carrier gas stream. Heating the at least one screen preferably comprises supplying electric current in an electrically conductive screen. Thus, disposing at least one pervious screen may comprise disposing a woven wire mesh, or disposing a sheet of metallic felt. In one preferred method, directing the carrier gas stream to a detector comprises directing the carrier gas to an ion mobility spectrometer.

A primary object of the present invention is to provide a compact, inexpensive, durable particle preconcentrator suitable for promoting the detection of trace amounts of airborne targeted substances, such as explosives, narcotics or chemical agents.

A primary advantage of the present invention is that it is operable repeatedly with a short cycle time.

Another advantage of the invention is that it is compact and durable, and suitable for use in conjunction with personnel screening at airports and the like.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

Figure 1:
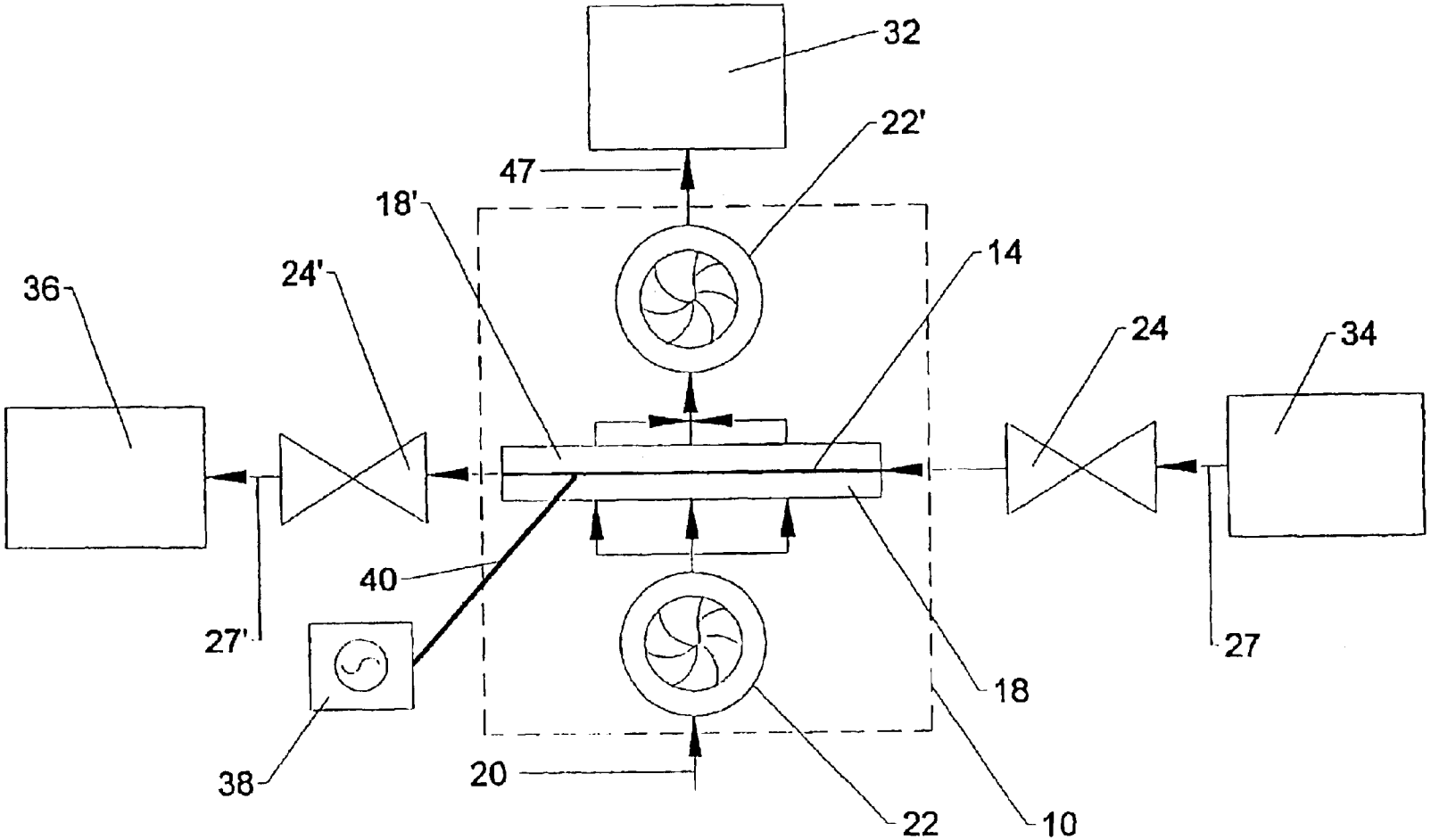
FIG. 1 is a diagrammatic view of a preferred embodiment of the present invention.

DESCRIPTION OF THE PREFERRED EMBODIMENTS (BEST MODES FOR CARRYING OUT THE INVENTION)

The invention relates to an apparatus and method for pre-concentrating particles from a regime of low concentration for presentation to a particle detector. More specifically, the preconcentrator apparatus and method of the invention collects particles entrained in low concentrations within a moving gas or airstream, accumulates the particles, and then releases them to a known detection or measurement device, thereby permitting the detector or measurement device to detect and/or evaluate the presence of target particles in the air stream at or below the ordinary lowest threshold of reliability of the detector. A vapor particle concentrator is provided to collect by adsorption vapor and small particles from a large volume gas stream for later release or desorption into a low volume carrier gas. The invention may be practiced in airport terminals and the like, for rapid consecutive screening of large numbers of people or items.

The present invention finds ready beneficial use as a component of a larger explosive or narcotics detection system or method. With the increasing use of explosives and chemical agents as a means of terrorism and the on-going use and transportation of illicit narcotics and other drugs, governments and industry have a compelling need to be able to detect the presence of persons and/or items which have come in contact with these substances. Examples of practical applications of the invention include, but are not limited to, the screening of passengers and baggage at airports, train terminals, and the like for explosives residues for the purpose of detecting concealed bulk quantities of explosives and/or persons who recently have handled explosives; the screening of visitors at penitentiaries, courthouses, and other secure facilities for drugs or other contraband substances; and detection of explosives in packages at postal or package handling facilities. The invention may also find use as a component in detection and screening apparatus or methods useable in industrial facilities, such as a pharmaceutical or nuclear facility, to prevent the smuggling of controlled substances in or out of the facility.

The foregoing is by way of practical examples, however, and it will be immediately apparent to one or ordinary skill in the art that the invention is beneficial in nearly any circumstance, for example in laboratory research, where it is desired to collect low concentrations of a targeted type of particle from ambient air or from a moving gas stream, and concentrate the particles for detection or measurement. In this disclosure and in the claims, "particle" means particulate matter of nearly any size, especially particulates sufficiently small as to be readily airborne, and includes but is not limited to droplets or dry motes, vapors, large molecules, and solid particles. "Target particles" or "target substance" refers to the particular type of particles sought to be preconcentrated by the practice of the invention, and includes, by way only of example, explosives, drugs, nuclear material, and the like. "Contraband substance" refers to a target substance that is illegal or undesirable. "Screen," unless otherwise indicated, means a partition or panel that is pervious to moving gas. "Gas" includes but is not limited to air.

Broadly described, the invention includes one or more gas-pervious screens disposed across a stream of moving gas, typically but not necessarily ambient air, in which the target particles are suspended or entrained in comparatively low concentrations. The gas stream passes through the screen so that at least some of the target particles are adsorbed or stuck upon the screen. A means, such as a valve, for interrupting the gas stream through the screen is provided, whereby the flow through the screen may be interrupted. The broadly described invention further includes a means, such as a fan or compressor, for generating a cross-flow of a carrier gas, such as filtered air, parallel past the screen to dislodge at least some of the target particles adsorbed upon the screen and entrain them into the carrier gas stream for transportation from the screen, typically to a detector. The invention also includes means and steps for controllably heating the screen and controllably interrupting or initiating the flow of the carrier gas stream.

Figure 2:
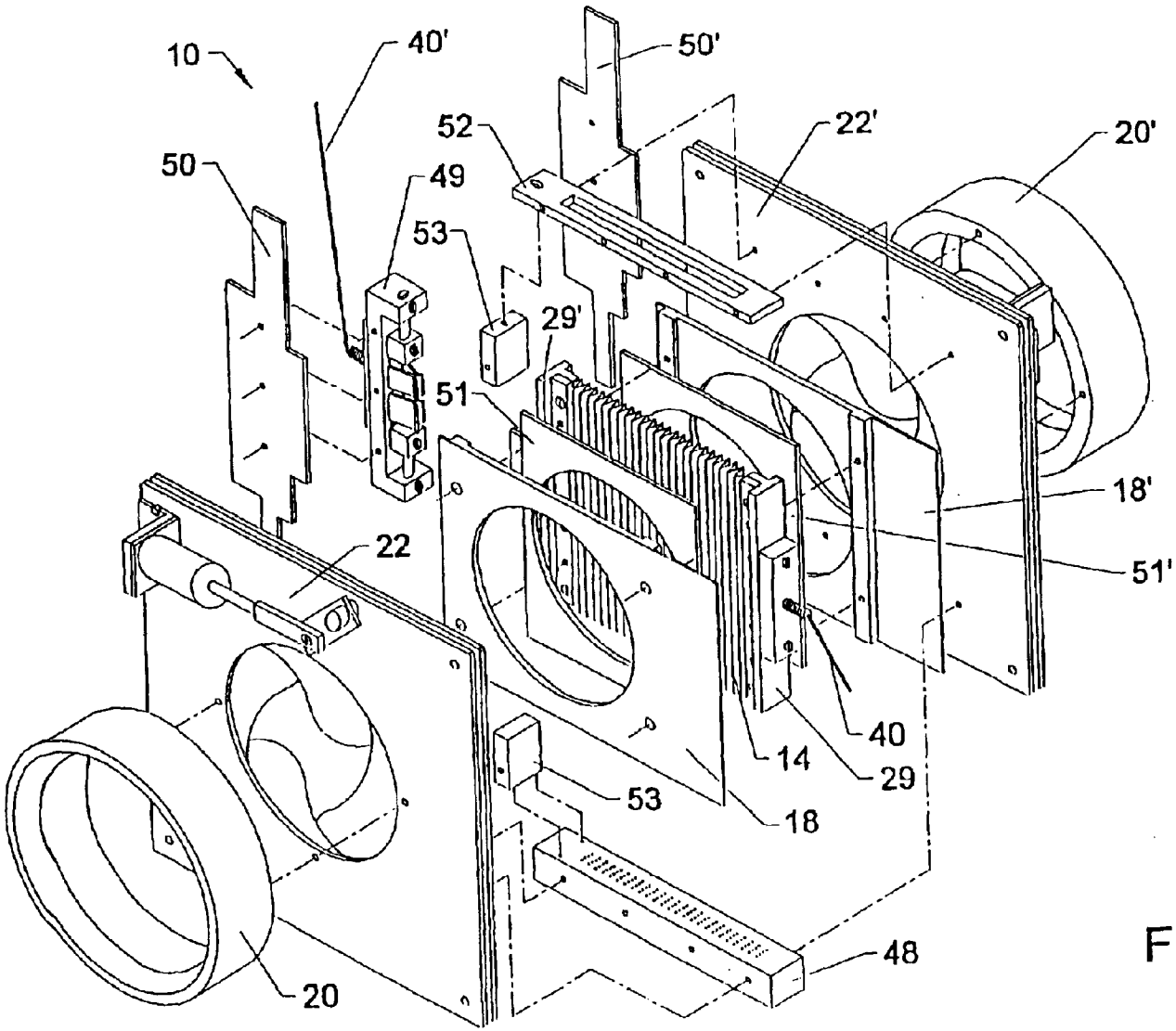
FIG. 2 is an exploded perspective view of one embodiment of a preconcentrator assembly according to the present invention.
Figure 3:
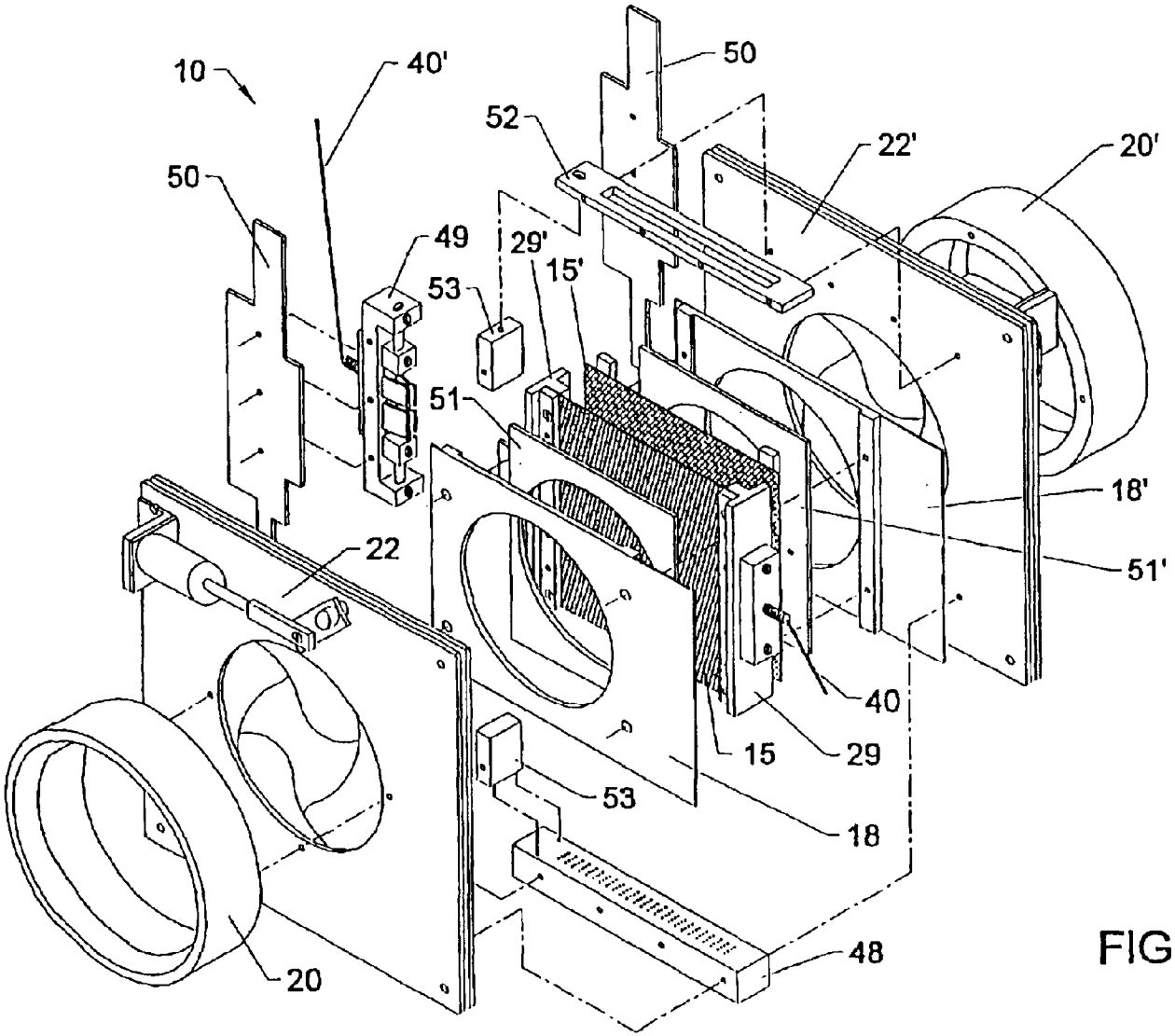
FIG. 3 is an exploded perspective view of an alternative embodiment of a preconcentrator assembly according to the present invention.

FIGS. 1–3 show the preconcentrator assembly 10 for collecting (adsorbing) vapor and small particles from a large volume gas stream for later release (desorbing) into a low volume carrier gas. In particular, preconcentrator assembly 10 can be used in conjunction with detection devices that determine the presence of explosives, drugs (e.g., narcotics) and chemical agents, notably detectors of relatively inexpensive, off-the-shelf availability. In this specification, reference is made to various types of "particle" detectors, but again it is understood that many types of particle detectors more specifically are vapor detectors; in this specification "particle" includes "vapor." Current detection devices rely on a relatively high concentration of particles. When a large air flow is sampled, the particles become very dilute making their detection difficult. But current detection devices cannot process the large amounts of air flow required for particle detection schemes that sample humans, luggage, motor vehicles, and the like at a reasonable rate. A preconcentrator assembly becomes a necessity when large flow rates are required. Preconcentrator assembly 10: (1) effectively collects extremely small amounts of particles from a large volume air flow; (2) retains the collected sample; and (3) releases the collected particles into a low-volume carrier gas for detection. For a preconcentrator to operate as an effective part of a sampling system, it must perform these functions efficiently and reliably with a simple design.

Referring to FIG. 2, the preconcentrator assembly 10 preferably includes at least one screen 14 and various other components disposed between a pair of main adsorb valves 22, 22'. Main adsorb valves 22, 22' are ultimately secured together so that the entire assembly 10 is generally of a layered or sandwich-like configuration, with adjacent components in compressed serial parallel arrangement as suggested by the drawings. Intake duct 20 and exhaust duct 20' permit a moving gas stream to enter and exit the overall assembly 10. The two main flow adsorb valves 22, 22' are used to interrupt and control passage of the gas stream perpendicularly through the screen 14. In the preferred embodiment, the screen 14 is electrically isolated from the adsorb valves by a pair of parallel insulator plates 18, 18' fashioned from an electrically insulative material such as a polyamide or the like.

The portion of the assembly 10 including the plates 18, 18', the screen 14, and the adsorb valves 22, 22' typically is disposed within a plenum (not shown) or in serial connection with ducts 20, 20' of generally ordinary construction, whereby the flow of the large volume gas stream is contained and directed to and through the assembly 10. Performance of the invention is maximized, however, when the length of the duct 20 leading to the screen 14 has the shortest length practicable.

A broad understanding of the preferred embodiment of the apparatus is promoted by characterizing the apparatus as a "screen assembly" which is slidably removable from within a "valve assembly." The screen assembly comprises at least one screen 14 in electrical and mechanical attachment to a pair of contact blocks 29, 29'. The physical integrity of the screen assembly is provided by the pair of electrical insulator plates 18, 18' being attached to opposing sides of both contact blocks 29, 29'. The insulator plates 18, 18' hold in place a pair of thermal insulator panels 51, 51', with one of each of the insulator panels located on opposing sides of the screen 14 between the screen 14 and a respective one of the plates 18, 18'.

The valve assembly is a housing into which the screen assembly is placed in parallel relation. The valve assembly preferably includes the adsorb valves 22, 22', a manifold block 48, an exit block 52, a pair of spacer blocks 53, a contact clip 49 and at least two insulator shims 50, 50'. The manifold block 48 and the exit block 52 preferably are disposed parallel to each other, and both blocks 48, 52 are fixedly attached to the interior sides of each of the adsorb valves 22, 22' to hold the adsorb valves together in spaced-apart relation. Respective spacer blocks 53 also are attached to either the manifold block 48 or the exit block 52 and to both adsorb valves 22, 22' to secure the valve assembly together. The contact clip 49 is secured between aligned edges of the adsorb valves 22, 22', but is electrically insulated from the adsorb valves 22, 22', e.g. by the use of nylon screws and the presence of the insulator shims 50, 50', one each of which is situated between either side of the contact clip 49 and the respective adjacent adsorb valve 22 or 22'.

In the foregoing configuration, the screen assembly can be slipped in and out from within the valve assembly. The insulator plates 18, 18' mounting the screen 14, contact blocks 29, 29' and insulator panels 51, 51' simply slide closely adjacent past inside faces of the adsorb valves 22, 22'. The insulator plates 18, 18' can be slipped into the space between the adsorb valves 22, 22' until the plates 18, 18' "bottom out" against the spacer blocks 53. When the valve assembly is thus fully inserted, the back contact block 29' engages with the contact clip 49 to provide an electrical connection therebetween. When the screen assembly is in the valve assembly, the opposing edges of the insulator plates 18, 18' may ride and rest upon the manifold block 48 and the exit block 52. The insulator plates 18, 18' accordingly function not only to maintain the screen 14 and contact blocks 29, 29' in proper position between the adsorb valves 22, 22', but also serve to electrically isolate the screen and contact blocks from the desorb valves and the manifold and exit blocks 48, 52. An advantage is that the screen assembly thus is easily removable and replaceable for cleaning and maintenance.

Adsorb valves 22, 22' preferably comprise "iris" or diaphragm shutters substantially similar to the diaphragms used in optical camera systems. The use of diaphragm shutters as gas valves in the preconcentrator apparatus permits the flow of gas through the assembly 10 to be controllably interrupted quickly, but without requiring the lengthy intra-valve flow path commonly encountered with ordinary gas valve devices. Diaphragm shutters as adsorb valves 22, 22', operating within very narrow housings as seen in FIGS. 2 and 3, reduce the flow path length and thus minimize the surface area upon which target particles may prematurely attach prior to adsorption upon the screen 14. Most known gas control valves have a relatively long flow path length (ten to twenty times more) compared to a diaphragm shutter valve of the same diameter. These flow path lengths are very important when attempting to preconcentrate low concentrations of adhesive particles, when premature adhesion of target particles to an upstream valve 22 may impair the preconcentrator's ability to adsorb particles upon the screen 14. Moreover, diaphragm shutters are capable of millions of cycles before failure, which is a concern with repetitive use.

The screen 14 is disposed between the pair of parallel, preferably substantially planar insulator panels 51, 51'. Insulator panels 51, 51' preferably are fashioned from an electrically insulative substance, such as silica glass, which withstands high temperatures. The insulator panels 51, 51' provide thermal protection to the insulator plates 18, 18', as the screen 14 in the preferred embodiment is heated during operation of the invention. Insulator plates 18, 18' hold the insulative panels 51, 51' in place parallel to the screen 14 and in parallel spaced relation from the valves 22, 22'. In the practice of the invention, the screen 14, the plates 18, 18', and the panels 51, 51' are positioned across the flow direction of a controlled, interruptible, large volume gas stream. The insulator plates 18, 18' and the insulative panels 51, 51' have large centrally located openings therein to permit a large volume air flow to move therethrough, that is, normal to the planes of the plates 18, 18' and panels 51, 51'. When the apparatus is properly assembled, central openings in the plates 18, 18' and in the panels 51, 51' are substantially aligned with colinear axes of the adsorb valves 22, 22'.

The screen 14 is substantially pervious to moving gases such as air. Preferably, the screen 14 is fashioned from an electrically conductive material, but which material is sufficiently resistive as to generate heat when electrical current is supplied. In the preferred embodiment as shown, the screen 14 comprises a sheet of metal fiber felt material, such as one of the metal fiber matrices manufactured and sold by Bekaert Corporation, Marietta, Ga., USA, a subsidiary of Bekaert Fibre Technologies, Zwevegem, Belgium, under the trademarks Bekipor® ST 60AL3, Bekipor® ST 60AL3S, and Bekipor® ST 60AL3SS. As best seen in FIG. 2, a metallic felt screen 14 preferably is configured with zig-zag pleats to increase the collection surface area presented to the moving gas flows and reduce the pressure drop through the screen during the adsorb flow. Because metallic felts are highly efficient collectors, a single metallic felt screen 14 preferably is used in the invention. For example, but not by way of limitation, in one embodiment, the screen 14 comprises a sheet of Bekipor® ST AL3 metallic felt of about 130 square inches, folded in an "accordion" fashion to form a pleated sheet about 7.0 inches on a side with a pleat peak-to-peak height of about 0.5 inches and a pleat peak-to-peak separation of about 0.25 inches.

Alternatively, the screen 14 may comprise one or more sections of woven wire mesh 15, 15', as illustrated by FIG. 3. The embodiment of FIG. 3 is substantially similar in most respects to the embodiment of FIG. 2, except that FIG. 3 illustrates that at least two parallel screens 15, 15' may desirably be employed in alternative embodiments of the invention. Elements and components which occur in FIG. 3 and which are the same or similar to corresponding elements in FIG. 2 are labeled with the same label numbers. In alternative embodiments where at least one woven wire mesh 15 is used, the mesh may have, for example, a wire diameter of 0.015 inches, and 20 wires per inch (20 mesh). A plurality of two to five woven wire mesh screens 15, 15' may be used, with two or three parallel woven wire 20 mesh screens 15, 15' normally being adequate for the alternative embodiment. In alternative embodiments of the invention not incorporating a heatable screen, the screens 15, 15' may be fashioned from non-conductive materials pervious to gas, such as paper or cloth.

Continued reference is made to FIGS. 2 and 3. Spacer blocks 53 are provided which are connected to both adsorb valves 22, 22' to hold the valves in spaced parallel relation. Each of the insulative plates 18, 18' is disposed in contact with the contact blocks 29, 29' so that the contact blocks 29, 29', which hold the screen 14, are electrically isolated from the adsorb valves 22, 22'. Insulative panels 51, 51' are in closely spaced relation to the screen 14 on each side thereof, to thermally insulate the screen 14 and maintain it in position during operation of the invention. Preferably, the insulative panels 51, 51' do not contact the faces of the screen 14, but the distance between each insulative panel 51, 51' and the face of the screen 14 is minimized in order to maximize the ratio of screen surface area to the internal volume of the assembly 10.

The screen 14 (or screens 15, 15') is mounted in the assembly 10 by means of contact blocks 29, 29' attached to the plates 18, 18'. The contact between the plates 18, 18' and the manifold and exit blocks 48, 52 provides the physical connection of the screen 14 to rest of the assembly 10. Contact blocks 29, 29' hold the sides of the screen 14 and are electrically conductive, whereby an electrical potential applied across the two blocks 29, 29' supplies a current flow through the screen from block 29 to block 29'. A contact clip 49, fixed between the desorb valves 22, 22' is provided for supplying electrical current to the back contact block 29'. The contact clip 49 is removably engageable with sockets and/or contacts on back contact block 29'. The contact clip 49 and the front contact block 29 each mount an electrical lead 40 or 40' connected thereto by which current can be supplied. Thus, with clip 49 in electrical connection with the back block 29', voltage and current are supplied through the series circuit including power leads 40, 40', the contact blocks 29, 29' and the screen 14 by means of conventional outside voltage sources such as a conventional AC power source 38 (FIG. 1). DC power sources may also be used, for example, to promote portability.

In the complete assembly 10, the manifold block 48 is situated along a third edge of the screen 14 extending perpendicularly to the contact blocks 29, 29', but the manifold block does not come in actual contact with the screen 14 or the contact blocks 29, 29'.

Manifold block 48 is fully penetrated, along nearly its complete length, by a series of numerous uniformly spaced nozzle holes. The exterior face of the manifold block 48 is in fluid communication with the upstream secondary ducting 27 (FIG. 1) which delivers the carrier gas stream. Carrier gas supplied to the assembly 10 from the carrier gas source 34 is introduced along the full width of the screen 14 by the action of the spaced nozzle holes so that a substantially even, uniform flow of carrier gas passes laterally across the full surface of both faces of the screen 14. Most preferably, in alternatives employing a pleated sheet metallic screen 14, at least one nozzle hole is provided corresponding to and aligned with each pleat or channel in the screen 14. The manifold block 48 thus receives the channeled flow of carrier gas from the upstream secondary ducting 27, and distributes the carrier gas to an even, sheet-like flow across the full width of the screen 14.

Along the fourth edge of the screen 14, opposite the manifold block 48, is the supply gas exit block 52. Exit block 52 features an oblong slit or aperture, or alternatively any number of apertures, which permit the passage of carrier gas from the space between the insulator panels 51, 51' to the exterior of the assembly, e.g. via a secondary exhaust duct 27' in communication with a downstream desorb valve 24', as indicated by FIG. 1. From the downstream desorb valve 24' the carrier gas is directed on toward the detector 36.

Manifold block 48 and exit block 52 are secured to the spacer blocks 53. The manifold block 48, the exit block 52, and the spacer blocks 53 in turn are attached to the desorb valves 22, 22' to provide structural integrity to the apparatus. The two contact blocks 29, 29', the manifold block 48, the exit block 52 and the two insulator panels 51, 51' in the assembled apparatus thus define there within a narrow parallelepiped space in which the screen 14 is suspended. The first, main gas stream flows through this space via the generally coaxially aligned central holes in the panels 51, 51' and in the plates 18, 18' and through the diaphragm shutters 22, 22'. The carrier gas cross-flows through the space, from the manifold block 48 to the exit block 52, generally parallel between the insulator panels 51, 51'.

Attention is invited to FIG. 1, schematically diagraming the principal components and function of the apparatus of the invention. As mentioned, the plates 18, 18', screen 14 and adsorb valves 22, 22' preferably and normally are disposed within or in fluid communication with ducting 20 which contains and directs the movement of a first or main gas stream toward the upstream adsorb valve 22. If the upstream adsorb valve 22 is open, the moving gas stream is free to flow through the opening in the upstream insulative plate 18, thereby permitting the gas stream to pass perpendicularly through the screen 14 and then on through the downstream plate 18'. When the upstream adsorb valve 22 is open, the downstream adsorb valve 22' is open, so that the gas stream flowing and diffusing through the screen 14 is free to exhaust through the downstream plate 18' in an exhaust steam 47 through the duct 20' and on out of the assembly 10 of the invention. In the preferred embodiment, the adsorb valves 22, 22' are closely adjacent to respective plates 18, 18' so that the gas stream flows in rapid succession through the upstream adsorb valve 22, the upstream plate 18, the screen 14 and the downstream plate 18', with minimal travel distance between these components. The adsorb valves 22, 22', and particularly the upstream adsorb valve 22, function therefore, as a means for interrupting the passage of a large volume gas stream perpendicularly through the screen 14.

Continued reference to FIG. 1 shows that the apparatus is provided with secondary ducting 27 disposed so as to contain and direct the flow of a carrier gas stream from a source 34 to the manifold block next to the screen 14. Carrier gas then flows through the manifold block and parallel across the faces of the screen 14, past the screen 14 parallel between the insulative plates 18, 18'. An upstream desorb valve 24 is disposed in the secondary duct 27' upstream from the screen 14, while downstream desorb valve 24' is disposed within the downstream portion of the secondary duct 27. Because the carrier gas stream does not initially carry any target particles, but rather is an inert "cleaning" gas, the upstream desorb or carrier gas inlet valve 24 need not be a diaphragm shutter, but may be a conventional gas valve, such as a ball valve. However, during the practice of the invention, the carrier gas exiting away from the screen 14 has target particles entrained therein that have been dislodged from the screen 14. It is desirable to minimize the number of target particles that stick to the downstream secondary duct 27' or are otherwise diverted or prevented from reaching the detector 36. Accordingly, the distance between the screen 14 and the detector 36 is minimized as practicably possible, and the carrier gas outlet valve 24' optionally comprises a diaphragm shutter such as previously described with reference to the adsorb valves 22, 22'. Alternatively, gas outlet valve 24' is a gate or ball type valve.

The adsorb valves 22, 22' and desorb valves 24, 24' are used to channel two distinct gas streams: by means of the adsorb valves 22, 22' a first moving gas stream is controllably directed perpendicular through the screen 14; by means of the desorb valves 24, 24', a separate carrier gas stream is directed in a cross-flow parallel to screen 14. In the practice of the invention, the adsorb valves 22, 22' are preferably open only when the desorb valves 24, 24' are closed, and the desorb valves 24, 24' are open only when the adsorb valves 22, 22' are closed, as further described below.

A method and practice of the invention are understood with combined reference to FIGS. 1 and 2. The method and operative routine have two fundamental phases: the "adsorb" phase during which target particles are preconcentrated by their being caught and adsorbed upon the screen 14, followed by the "desorb" phase during which the preconcentrated particles are removed from the screen 14 and directed to a detection or measuring device 36. The movement of gas streams in the practice of the invention is generally indicated by the various directional arrows in FIG. 1. At the inception of one preferred method and operation of the apparatus, the adsorb valves 22, 22', and the desorb valves 24, 24' are closed, isolating the screen 14 against inadvertent or premature exposure to contaminants.

At the beginning of the adsorb phase, a means for inducing a moving first, or main, gas stream is actuated to induce a flow of gas, typically ambient air. The moving first gas stream is blown past the item, person, or other sample to be tested for the presence of target substances, and then on into the short duct 20 leading to the screen 14. The means for inducing the moving first gas stream may be a known type of fan 32 with which to blow ambient air, or may be a source of compressed filtered air, or a filtered inert gas or gas mixture, depending upon the particular application of the invention. The fan 32 for generating the large volume gas stream flow may be positioned "upstream" of the assembly 10, nearer the first adsorb valve 22, to "push" gas toward the assembly, but may also, and in many applications may preferably, be disposed "downstream" from the second adsorb valve 22', to "suck" or "pull" the gas stream through the assembly 10, as indicated in FIG. 1. The overall intention of the invention is to generate the necessary gas pressure differential across the assembly 10, by any suitable means, to provide for a large volume first gas stream flow through the assembly and generally perpendicularly through the screen 14.

The volume discharge of the first moving gas stream is widely variable and may be adapted to the particular use of the invention, and in consideration of the size of the screen 14, the speed with which the preconcentration must be accomplished, and other factors. In a typical application within, for example, a device for testing passengers boarding aircraft, the volume of the moving gas stream comprising the "adsorb flow" may be from about 64 $ft^3$/min (30 liters/sec) to about 340 $ft^3$/min (160 liters/sec). The foregoing volume discharge figures are by way of example, the only limiting factor to larger flows being the pressure drop through the assembly 10 and screen 14 and the ability of an auxiliary exhaust blower (optional) to develop a given flow with a given pressure drop. In the case of a two horsepower fan 32, for example, the apparatus of the invention may be devised to operate with a static pressure drop of about 5 inches.

The moving first gas stream, as it blows past the item to be evaluated, dislodges particles from the item, including any particles of the target substance that may be present thereon, whereby the particles become entrained in the moving gas stream. In alternative embodiments, the moving gas stream, with target particles already mixed therein, may be released under pressure from a containerized source of gas to be evaluated.

When the means for inducing the first gas stream movement is activated, as by the actuation of fan 32, the adsorb valves 22, 22' are opened to permit the moving first gas stream, with target particles entrained therein, to flow toward the screen 14. The desorb valves 24, 24' remain closed to prevent gas movement into or through the auxiliary ducting 27, 27'. Preferably, the distance from the source of the target particles to the screen 14 is minimized to reduce target particles loss from premature adhesion to the walls of duct 20, etc.; the service of a diaphragm shutter as the upstream adsorb valve 22 aids in the minimalization of the moving gas stream flow path length.

The moving first gas stream passes through the upstream adsorb valve 22 and perpendicularly to the screen 14, and passes through the screen 14. By placing the screen or screens across the large volume air stream, the first gas stream must pass through the screen 14 to exit the preconcentrator assembly 10. As the gas stream passes through the screen 14 at least some of the particles entrained in the gas stream are caught by the screen, as by absorption and/or adhesion. The screen 14 thus acts essentially as a filter or collector for catching particles, including target particles, and removing them from the moving gas stream. Thus, particularly with the use of a metallic felt matrix screen, the probability of particles exiting the apparatus of the invention without striking and "sticking" to the screen 14 is low. Most explosives particles are, for example, between about 10 microns and about 100 microns in diameter; the preferred screen 14 used in the invention is a metal felt with a minimum pore size of 60 microns, and thereby preconcentrates explosive particles for detection. Other applications of the invention may incorporate screens which collect smaller particles, or pass larger particles than 60 microns.

Particles borne by the moving gas stream continue to accumulate upon the screen 14 for the duration of the stream's passage through the screen. The duration of the large volume flow of the moving gas stream is dependent upon the application for which the invention is being used. In an airport passenger screening situation, by way of non-limiting example, the moving gas stream is allowed to flow through the screen 14 for approximately 10 seconds, which we have determined to be an adequate duration to permit sufficient collection of target particles upon a screen 14 of about 130 square inches. The cumulative total volume of gas passed through the screen 14 during a single typical adsorb cycle in such an instance is about 51 $ft^3$ (1,500 liters). In situations where rapid cycle time is of primary concern (such as at airports), more than one preconcentrator assembly 10 may be used concurrently, with two or more assemblies ducted in parallel to permit a shorter "adsorb" time. For example, two assemblies 10 configured in parallel flow can process a given volume of a moving gas stream at twice the rate of a single assembly 10, permitting the time duration of flow to be reduced by half.

At the timed conclusion of the adsorb phase, during which target particles are collected and retained upon the screen 14, the adsorb valves 22, 22' are closed to interrupt the passage of the first gas stream through the apparatus. The fan 32 may, but is not necessarily, also turned off. The passage of the moving gas stream through the screen 14 is terminated, leaving a quantity of particles adsorbed upon the screen 14.

Accordingly, a dilute sample of target particles are collected from the large volume moving gas stream, and preconcentrated in a much smaller volume upon the screen 14. Retained upon the screen 14, the preconcentrated target particles are in a position to be delivered directly to a detector 36 by means of a cross-flow of a separately originated cross-flow of carrier gas.

The desorb phase of the practice of the invention is characterized mainly by the generation of a cross flow of a carrier gas past the screen 14. The cross flow of carrier gas removes the accumulated particles from the screen 14 for transport to a detection unit 36. In the preferred embodiment, the desorb phase also includes the heating of the screen 14 to promote the desorption of the accumulated particles from the screen 14. The performance of the invention is dramatically improved by the incorporation of a heatable screen 14, although inexpensive alternative embodiments need not necessarily use a heatable screen 14 element. As previously detailed herein, the screen 14 in the preferred embodiment is electrically conductive metallic felt or woven wire mesh, such that resistance to electrical current through the screen 14 provides the desired elevation in screen temperature. Alternative modes of heating the screen 14 are within the scope of the invention, as are embodiments utilizing non-conductive screens which do not involve the heating step. Alternative, suitable means and modes of heating the screen 14 include, for example, the use of quartz lamps and lasers to provide rapid or "flash" intermittent heating of the screen. In addition, the hot carrier gas can serve this purpose.

In the preferred embodiment, after the adsorb valves 22, 22' are closed to interrupt the flow of the main gas stream through the screen 14, the screen 14 is heated. A voltage is applied to the screen 14 by way of the electrically conductive leads 40, 40', contact clip 49 and contact blocks 29, 29' to supply electric current through the screen 14. (Screen 14 and contact blocks 29, 29' are electrically insulated from the other principal components of the assembly 10 by the insulator plates 18, 18'.) Preferably, alternating current is used, supplied through wiring from a conventional AC power source 38. In one embodiment using for a screen 14 a sheet of metallic felt about 130 square inches, AC current at 18 volts and 500 amperes is supplied to the screen. The electrical resistance in the screen 14 causes the screen to warm from room temperature to, for example, about 200° C. to promote desorption of the particles from the screen 14. The screen 14 warms rapidly, and the current is turned off after about 1–5 seconds.

While or immediately after the screen 14 is warmed, the desorb valves 24, 24' are opened to generate a cross-flow of carrier gas from a source 34 thereof to and parallel across the (preferably heated) screen 14. One of desorb valves, the carrier gas inlet valve 24, when open allows the carrier gas to flow from the source 34 into the confined space between the panels 51, 51'. The downstream desorb valve or carrier gas outlet valve 24' is operable to control the flow of carrier out the exit block 52, away from the screen 14 and toward the particle detector 36. This cross flow releases particles collected on the screen 14 and blows the released particles away from the screen 14 but parallel to it. The particles, including target particles, are released from the screen 14, become entrained in the carrier gas stream, and are carried immediately to the detector 36.

The carrier gas stream preferably is a low-discharge of inert gas or filtered air, which dislodges the particles from the screen 14 without introducing contamination into the system. The means for generating the cross-flow of the carrier gas may be a second fan 34, or alternatively may be a simple source of clean pressurized gas.

The carrier gas stream cross-flow discharge is considerably smaller than the first main moving gas stream. In one preferred embodiment, the low volume cross flow during the desorb phase is about 8.5 $ft^3$/hr (67 ml/sec). However, the useful discharge in other applications can range from near zero to values approaching the volumes used in the first main, moving gas stream. The discharge value for the carrier gas cross-flow is a function of, among other things, the particular type of detector 36 in use. The time duration of carrier gas cross-flow also depends upon the particular application of the invention. In one preferred embodiment, the cross-flow lasts from about one to about five seconds.

There is an advantage in making the time duration of the carrier gas cross flow comparatively short. The best sample concentration occurs at the very beginning of the cross flow out of the space between the panels 51, 51', sometimes called the "plug flow." Plug flow is the phenomenon whereby a bulk volume of gas is moved from one location to another with little mixing within that volume. The invention's performance is enhanced when a plug flow is delivered from the screen 14 to the detector 36.

The invention also offers the advantage of a carrier gas cross-flow parallel to the screen 14, rather than a flow of carrier gas through the screen. By employing a cross-flow, rather than through-flow, of carrier gas, the tremendous pressure drops that otherwise may occur through the screen 14 during the desorb phase are avoided. A large pressure drop during the desorb phase requires the use of a high-pressure discharge of carrier gas that overwhelms the capabilities of many standard detector devices. The carrier gas flow of the present invention may be generated using comparatively low pressures.

Target particles entrained into the cross-flowing carrier gas are carried directly to the detector 36. Detector 36 is any of the devices known for detecting and/or measuring particles and/or particle concentrations. The detector 36 preferably is an ion mobility spectrometer, particularly if the invention is to be used to detect particles of explosives. Ion mobility spectrometers are a device known in the art of detecting dilute quantities of particles. Other detectors suitable or adaptable for use in the invention include, without limitation: an Electron Capture Device (ECD), which can detect explosives but perhaps not narcotics; gas chromatograph, chemiluminescence device (both of which detection methods are less desirable for detecting particles of narcotics); mass spectrometer (suitable for detecting a wide variety of target particles, including explosives and narcotics); ITMS® (Ion Trap Mobility Spectrometer, for detecting both explosives and narcotics), and Thermo-Redox. The detector 36 provides to the operator a measurement of the concentration of target particles in the carrier gas stream. In one embodiment of the invention, the detector 36 is connected to an audible or visual alarm in the event target particles are detected above a predetermined concentration.

The detection (or non-detection) of target particles completes the desorb phase of the operation of the invention After the desorb cycle is completed, the desorb valves 24, 24' are closed and the adsorb valves 22, 22' may again be opened to initiate another preconcentration cycle, if desired.

Broadly summarized, therefore, the method of the invention includes the steps of disposing across the first gas stream at least one gas-pervious screen, so that the first gas stream passes through the screen and at least some of the particles are caught upon the screen; interrupting the passage of the first air stream through the screen; after interrupting the passage of the first gas stream, then generating a cross-flow of a carrier gas stream parallel past the screen, so that particles caught upon the screen are entrained into the carrier gas stream; and then directing the carrier gas stream to a particle detector.

Further detailed particulars of the design of the assembly 10 are within the understanding of persons of ordinary skill in the art. Known principles of design and engineering may be used to modify or adapt the apparatus of the invention to differing uses. The apparatus may be modified to account for, for example, the relationship between numbers of screens 15, 15' and resulting pressure drop in the large volume moving gas stream. The surface area of screen required to adsorb certain particles is correlated with the size (horsepower) of the fan 32 required for the large volume gas stream. Alternative embodiments employing a plurality of small wire mesh screens providing large surface areas and good particle collection also cause large pressure drops and require a higher-powered fan 32. The opposite is true for one open wire mesh, or metallic felt, screen 14.

Heating of the screens to release the vapors or particles is optional but very preferred. The duration of applying current to the screen 14 for heating directly impacts the release of target particles to be transported to the particle detector 36. Excessive heating can result in the loss of sample due to particle destruction. Therefore, adapted variations to the invention account for target particle chemistry to avoid destroying particles while heating the screen 14.

Various embodiments of the invention may desirably be provided with means and methods for cleaning the screen 14. After prolonged use, the screen 14 may become covered with nontarget debris, such as lint, hair, dust and the like, which may impair the performance of the apparatus. Embodiments of the invention may incorporate a screen 14 that may be slidably removable from between the panels 51, 51' to be cleaned of debris by rinsing, brushing, or blowing, and then slidably re-inserted into position for use. Alternatively, means may be provided for cleaning the screen 14 in situ, for example by reversing the direction of gas flow through the screen 14 to perform a "back flushing" of the screen. Still further, an automated mechanical brush or rake may be supplied periodically to sweep the face of the screen 14 free of accumulated debris.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

We claim:

1. An apparatus for concentrating vapor *or* particles entrained in a moving air stream said apparatus comprising:

at least one pervious screen disposed substantially perpendicularly to the air stream, whereby the air stream passes through said screen and at least some of the particles *or vapor* are caught upon said screen;

means for interrupting the passage of the air stream through said at least one screen;

[means for heating said at least one screen;] and means for generating a carrier gas stream cross-flow past said at least one screen, whereby particles *or vapor* caught upon said screen are entrained into the carrier gas stream.

2. An apparatus according to claim 1, further comprising a fan for inducing the movement in the air stream.

3. An apparatus according to claim 1 wherein said means for interrupting the passage of the air stream comprises at least one diaphragm shutter.

4. An apparatus according to claim 1 wherein said means for generating a crossflow of a carrier gas stream comprises a carrier gas outlet valve comprising, a diaphragm shutter.

5. An apparatus according to claim 4 wherein said at least one pervious screen comprises a plurality of substantially parallel screens.

6. An apparatus according to claim 4 further comprising means for heating the at least one screen.

7. An apparatus according to claim 6 wherein said at least one screen comprises an electrically conductive screen and said means for heating comprises means for supplying electric current in said screen.

8. An apparatus according to claim 5 wherein said screens comprise woven wire mesh.

9. An apparatus according to claim 7 wherein said screen comprises at least one sheet of metallic felt.

10. An apparatus according to claim 9 further comprising a means for detecting vapor particles entrained in said carrier gas stream.

11. An apparatus according to claim 10 wherein said means for detecting comprises an ion mobility spectrometer.

*12. An apparatus for detecting particles or vapor comprising a metallic felt screen in communication with a detector, wherein the detector can detect trace amounts of contraband.*

*13. An apparatus for detecting particles or vapor comprising:*

(*a*) *a metallic felt screen in communication with a detector and in communication with a main gas stream generator to generate a main gas stream, wherein the metallic felt screen is disposed such that it is substantially perpendicular to the main gas stream; and*

(*b*) *a carrier gas stream generator in communication with the metallic felt screen to present a carrier gas stream to the metallic felt screen, which carrier gas stream then continues to the detector.*

*14. The apparatus of claim 13, wherein the carrier gas stream generator, the metallic felt screen, and the detector communicate with one another by way of a gas flow path.*

*15. The apparatus of claim 14, wherein the gas flow path comprises a structure to contain and direct the carrier gas stream.*

*16. The apparatus of claim 14, wherein the gas flow path comprises a duct.*

*17. The apparatus of claim 13, wherein the carrier gas stream generator comprises a suction generator.*

*18. The apparatus of claim 13, wherein the carrier gas stream generator presents the carrier gas stream to the metallic felt screen in a cross flow.*

*19. The apparatus of claim 18, wherein the cross flow is parallel to the metallic felt screen.*

*20. The apparatus of claims 12 or 13, further comprising a heater to heat the metallic felt screen.*

*21. The apparatus of claims 12 or 13, further comprising an intake duct in communication with the metallic felt screen to intake and direct the main gas stream to the metallic felt screen.*

*22. The apparatus of claim 21, comprising an exhaust duct in communication with the intake duct to exhaust the main gas stream after it has been directed to the metallic felt screen.*

*23. The apparatus of claims 12 or 13, wherein the detector comprises an ion mobility spectrometer, an electron capture device, a gas chromatograph, a chemiluminescence device, a mass spectrometer, an ion trap mobility spectrometer, or a thermo redox device.*

*24. An apparatus for detecting particles or vapor comprising:*

*(a) an intake duct;*

*(b) a main gas stream generator;*

*(c) a metallic felt screen;*

*(d) an exhaust duct;*

*(e) a carrier gas stream generator; and*

*(f) a detector,*

*wherein the intake duct communicates with the metallic felt screen and with the exhaust duct to intake and direct a main gas stream to the metallic felt screen where the metallic felt screen is disposed such that it is substantially perpendicular to the main gas stream whereby the main gas stream passes through the metallic felt screen and at least some of the particles or vapor are caught upon the screen, whereafter the main gas stream is exhausted by the exhaust duct, and wherein the carrier gas stream generator communicates with the metallic felt screen and with the detector to present a carrier gas stream to the metallic felt screen, whereafter the carrier gas stream is directed to the detector.*

*25. A method of detecting particles or vapor on an item comprising:*

*(a) dislodging the particles or vapor from the item;*

*(b) adsorbing the dislodged particles or vapor to a metallic felt screen;*

*(c) desorbing the adsorbed particles or vapor;*

*(d) directing the desorbed particles or vapor to a detector; and*

*(e) detecting the desorbed particles or vapor.*

*26. The method of claim 25, wherein dislodging the particles or vapor from the item and adsorbing the dislodged particles or vapor to the metallic felt screen comprises:*

*(a) disposing the metallic felt screen such that it is substantially perpendicular to a main gas stream, wherein the main gas stream is induced past the item to dislodge the particles or vapor from the item;*

*(b) entraining the dislodged particles or vapor in the main gas stream; and*

*(c) directing the main gas stream having the entrained particles or vapor through the metallic felt screen, whereby the particles or vapor are adsorbed.*

*27. The method of claim 26, wherein the main gas stream is induced by a fan.*

*28. The method of claim 26, wherein desorbing the particles or vapor comprises generating a carrier gas stream and directing it to the metallic felt screen.*

*29. The method of claim 28, wherein the carrier gas stream is generated by suction.*

*30. The method of claim 28, wherein the carrier gas stream is directed to the metallic felt screen in a cross flow.*

*31. The method of claim 30, wherein the cross flow is parallel to the metallic felt screen.*

*32. The method of claim 26, wherein desorbing the particles or vapor comprises heating the metallic felt screen.*

*33. The method of claim 26, wherein the particles or vapor are detected by an ion mobility spectrometer, electron capture device, a gas chromatograph, a chemiluminescence device, a mass spectrometer, an ion trap mobility spectrometer, or a thermo redox device.*

* * * * *